United States Patent [19]

Pugach

[11] Patent Number: 4,659,682
[45] Date of Patent: Apr. 21, 1987

[54] RECOVERY OF NOBLE METAL VALUES FROM CARBONYLATION RESIDUES

[75] Inventor: Joseph Pugach, Ridgewood, N.J.

[73] Assignee: The Halcon SD Group, Inc., Little Ferry, N.J.

[21] Appl. No.: 752,697

[22] Filed: Jul. 8, 1985

[51] Int. Cl.$^4$ .................. B01J 38/68; B01J 31/40; C07C 51/56

[52] U.S. Cl. ..................... 502/24; 260/546; 260/549; 423/22; 502/28; 502/31; 502/33

[58] Field of Search .............. 502/22, 24, 28, 33; 423/22; 260/549, 546

[56] References Cited

U.S. PATENT DOCUMENTS

| | | | |
|---|---|---|---|
| 3,887,489 | 6/1975 | Fannin et al. | 423/22 |
| 4,131,640 | 12/1978 | von Kutepow et al. | 423/22 |
| 4,340,569 | 7/1982 | Davidson et al. | 423/22 |
| 4,340,570 | 7/1982 | Davidson et al. | 423/22 |
| 4,341,741 | 7/1982 | Davidson et al. | 423/22 |
| 4,363,765 | 12/1982 | Fiato et al. | 549/208 |
| 4,388,217 | 6/1983 | Hembre et al. | 562/607 |
| 4,434,240 | 2/1984 | Pugach | 502/24 |
| 4,440,570 | 4/1984 | Erpenbach et al. | 75/121 |
| 4,442,304 | 4/1984 | Erpenbach et al. | 560/232 |
| 4,473,655 | 9/1984 | Tsuhuda | 502/30 |
| 4,476,237 | 10/1984 | Porcelli | 502/31 |
| 4,476,238 | 10/1984 | Palmer et al. | 502/31 |
| 4,578,368 | 3/1986 | Zoeller | 502/28 |

FOREIGN PATENT DOCUMENTS

| | | | |
|---|---|---|---|
| 891231 | 5/1982 | Belgium. | |
| 18102 | 10/1980 | European Pat. Off. | |
| 81732 | 6/1983 | European Pat. Off. | |
| 0128439 | 12/1984 | European Pat. Off. | 423/22 |

Primary Examiner—P. E. Konopka
Attorney, Agent, or Firm—Harold N. Wells

[57] ABSTRACT

Heavy residues produced by noble metal catalyzed carbonylation reactions and containing Group VIII noble metals, particularly rhodium, are treated with reagents to precipitate solids containing substantially all of the noble metal contained in the residues. The solids may be further treated to concentrate the noble metals or they may be returned directly for reuse in the carbonylation reaction. Suitable reagents include aliphatic alcohols, carboxylic acids, and carboxylic acid esters. Preferred are branched-chain alcohols, especially tertiary alcohols; of the acids, acetic acid is particularly preferred; and of the esters, n-butyl acetate and ethylidene diacetate are preferred. Subsequent treatments with other solvents, e.g., alkanes, cycloalkanes, ethers, and aromatic compounds, may be used to further concentrate the rhodium content of the precipitated solids.

6 Claims, 1 Drawing Figure

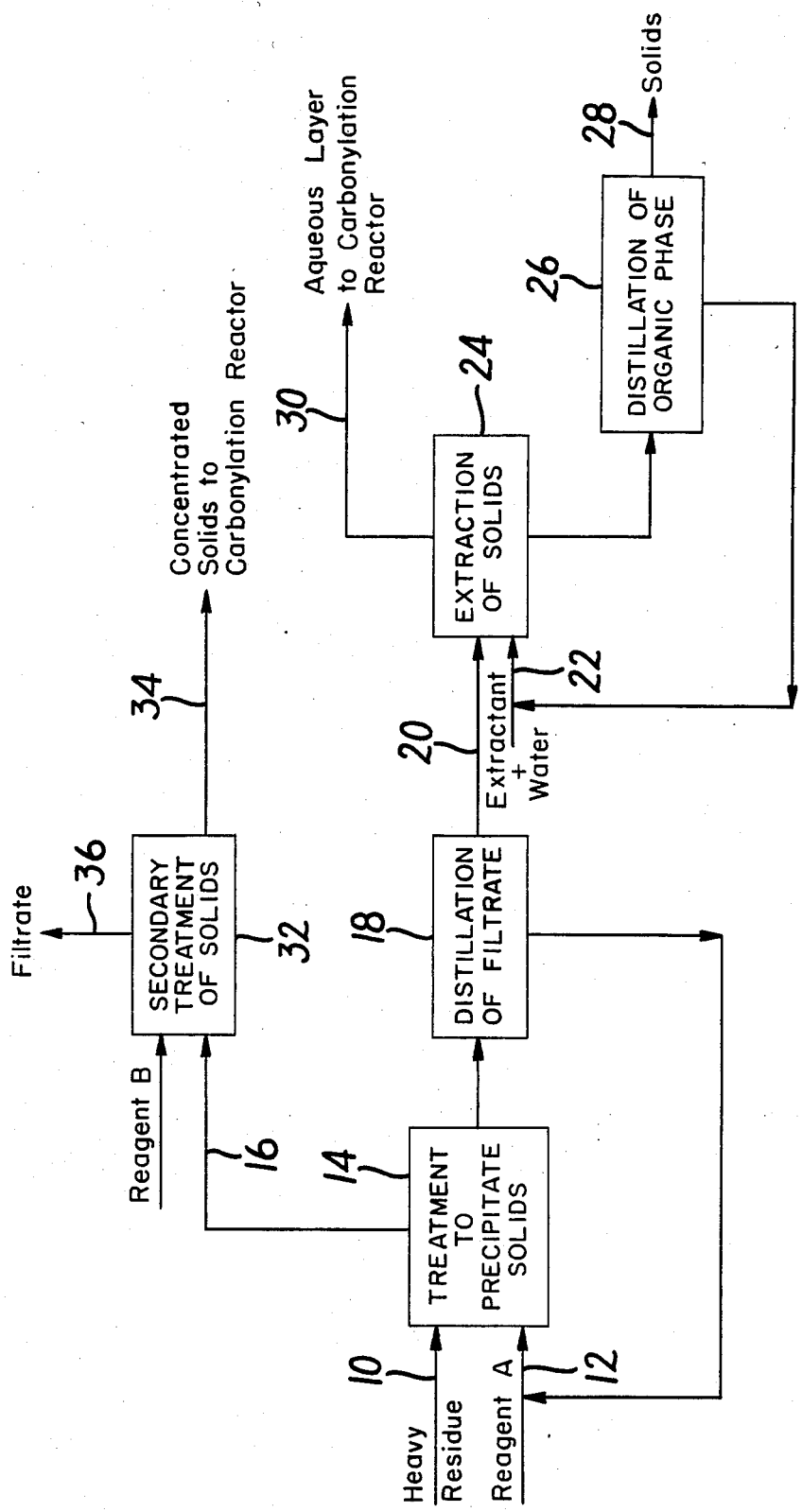

RECOVERY OF NOBLE METAL VALUES FROM CARBONYLATION RESIDUES

PRIOR ART

The invention relates to the carbonylation processes in which carbon monoxide is reacted with esters or ethers to produce anhydrides or higher molecular weight products. More specifically, the invention relates to the recovery for reuse of the noble metal values from residues formed in such carbonylation processes.

The carbonylation processes of interest differ from hydroformylation processes commonly employed industrially. Typically, in hydroformylation carbon monoxide and hydrogen are reacted with olefins to form higher molecular weight aldehydes and alcohols.

Both hydroformylation and carbonylation processes may produce heavy residues which must be removed to avoid detrimental effects on the reaction. The nature of these residues is not always precisely disclosed in the art, but they are thought to be polymers of the reaction products and/or byproducts. The chemical nature of the residues and their ability to hold the noble metal-containing catalyst would be expected to relate to the type of reaction being carried out. Thus, recovering the noble-metal values from such residues will require methods particularly suited to the origin of the residues. The methods to be disclosed herein are especially useful with respect to the processes described in U.S. Pat. Nos. 4,340,569; 4,340,570; and 4,341,741.

Recovery of noble metal values from hydroformylation residues is disclosed in a number of patents, which may reflect the extensive industrial applications of hydroformylation. However, since the residues are chemically related to the reactants, these patents are not considered as pertinent to the present invention as those pertaining to carbonylation generally or, more specifically, to the carbonylation of esters and ethers to form anhydrides.

Some disclosed methods for recovering noble metals from carboxylation processes have been directed to processes in which the presence of heavy residues has not been mentioned.

U.S. Pat. No. 3,887,489 discloses the recovery of rhodium from carbonylation processes which employ rhodium halide carbonyl complexes. Rhodium is precipitated from spent catalyst solutions by heating to 100°–190° C., preferably in the presence of an alkyl alcohol, and therafter converted to an active form for reuse. It should be noted that the process appears to have been applied to carbonylation of methanol to acetic acid, which produces no heavy residues. The principal objective of the rhodium recovery process was the separation from metallic corrosion products.

U.S. Pat. Nos. 4,131,640 presents still another method of precipitating rhodium from a rhodium carbonyl complex used for carbonylation of an alkanol or an olefin. The rhodium is deposited on a solid carrier, which is then treated to convert the rhodium back into a carbonyl complex. The precipitation occurs as a result of hydrogenation of the initial rhodium-containing solution at 20°–300° C. Again, the technique is used in carbonylation reactions which apparently produce a homogeneous product mixture and formation of residues is not noted.

In U.S. Pat. No. 4,442,304 the rhodium content of a catalyst solution obtained in the carbonylation of methyl acetate and/or dimethyl ether is separated by treating the solution with water, which dissolves the quaternary nitrogen or phosphorus compounds used as promoters in the process. The precipitate is subsequently treated with aliphatic ethers to remove the organic contaminants. In an apparently related patent, U.S. Pat. No. 4,440,570, the water treatment of the '304 patent is used, but the precipitated residue is to be refined to recover the noble metal.

Residues from a carbonylation process for preparing acetic anhydride may be treated with methyl iodide and aqueous hydrogen iodide to extract rhodium, as disclosed in U.S. Pat. No. 4,388,217. Such a process provides a solution of rhodium, rather than a solid containing it. A similar process is disclosed in Belgian Pat. No. 891,231.

A solution containing dissolved rhodium derived from the reaction of carbon monoxide and hydrogen with alcohols may be treated with a crown ether, an alkaline cesium salt and water to recover the rhodium by precipitation, as shown in U.S. Pat. No. 4,363,765.

Still another method of removing rhodium from a carbonylation solution is found in EP No. 18102. Silica and a silicon compound are reacted to form a product capable of absorbing rhodium from a solution.

A two-step separation of volatile materials from a carbonylation reaction mixture is shown in EP No. 81732. No treatment for recovery of the rhodium content is applied prior to recycle of the residual liquid.

The recovery of rhodium or other noble metal catalysts from the residues formed in the carbonylation of esters or ethers to form anhydrides has been the subject of commonly-assigned U.S. Pat. Nos. 4,340,569; 4,340,570; 4,341,741; 4,476,237; 4,476,238; and 4,434,240. In U.S. Pat. No. 4,340,569; 4,340,570; and 4,341,741 residues are treated with amines to facilitate subsequent extraction of the rhodium with aqueous acids. In U.S. Pat. No. 4,434,240 the residues are given chemical treatments to precipitate solids which contain substantially all of the rhodium, leaving the depleted residues for disposal. It was suggested that diluents such as methanol, glyme, and isopropanol could be used to dilute the residues prior to treatment with reagents to precipitate solids. However, such diluents did not in themselves result in precipitation under the conditions employed.

U.S. Pat. Nos. 4,476,237 and 4,476,238 pertain to the use of selective extraction to remove heavy residues preferentially, leaving rhodium behind. The preferred solvents had relatively poor solvent properties, and isopropanol and ethanol were shown to be such effective solvents that they were not selected.

The present invention is directed to improved techniques by which such residues be treated to recover their noble metal content.

SUMMARY OF THE INVENTION

The invention is a process for recovering rhodium from the heavy residues of rhodium-lithium catalyzed carbonylation reactions in which esters and ethers are combined with carbon monoxide in the presence of iodides to form anhydrides or other higher molecular weight products. The residue is separated from the carbonylation reaction mixture and then treated at above ambient temperatures, typically 50°–250° C., with a reagent capable of precipitating solids which contain substantially all of the noble metal contained in the residue. The solids may be further treated to recover the noble metals, but they may be returned directly to the carbonylation reactor and reused without further preparation.

Various reagents may be employed according to the invention. Specific embodiments include the use of aliphatic alcohols having 3-10 carbon atoms, particularly branched alcohols such as isopropanol, and especially tertiary alcohols such as t-butyl alcohol. Carboxylic acids having 2-10 carbon atoms, such as propionic acid, n- and i-butyric acids, and particularly acetic acid, are useful. Of the carboxylic acid esters, those having 3-10 carbon atoms, particularly butyl acetate and ethylidene diacetate, are preferred.

After precipitation, the solids containing the noble metal values may be further treated with solvents capable of removing a portion of the organic material while leaving the noble metal in the solids. The solvents may be selected from the group consisting of alkanes, cycloalkanes, aromatics, ethers, and cyclic ethers. Such a treatment can concentrate the noble metal values significantly and reject a portion of the residues.

In a complete process most of the rhodium is first recovered in a relatively small amount of solids as described above. The bulk of the remaining residues contain only a little rhodium, but they may be further treated with extractants, such as methyl iodide and aqueous hydrogen iodide, to complete the recovery of rhodium, after which the depleted residue may be purged.

BRIEF DESCRIPTION OF THE DRAWING

The sole FIGURE is a block diagram showing a process for recovering rhodium from heavy residues according to the invention.

DESCRIPTION OF THE PREFERRED EMBODIMENTS

The recovery of Group VIII noble metals, especially rhodium, from carbonylation and hydroformylation reaction mixtures has been of considerable interest to those skilled in the art. Of particular concern to the present inventor is the recovery of Group VIII noble metals, particularly rhodium, from catalysts used in the carbonylation of a carboxylic ester or an alkyl ether to an anhydride, or to higher molecular weight products, especially the carbonylation of methyl acetate or dimethyl ether to acetic anhydride. In another aspect, the invention relates to recovery of rhodium-lithium catalysts used for the carbonylation in the presence of hydrogen of methyl acetate and/or dimethyl ether to ethylidene diacetate. These processes have been described in depth in British Pat. Nos. 1,468,940 and 1,538,782, and are summarized in U.S. Pat. Nos. 4,340,569; 4,340,570; and 4,341,741.

The invention broadly relates to the selective removal of the noble metals by precipitation from the heavy high-boiling residues, produced by carbonylation reactions, with or without hydrogen being present. These heavy residues are complex, and their chemical composition is not fully characterized. Where they have been produced during the carbonylation of esters or ethers, they are known to contain high molecular weight compounds with organic carbonyl and acetate functions. If a sample of a carbonylation reaction mixture is flashed and concentrated, the residues which are recovered typically contain up to about 4 percent by weight rhodium after the volatile constituents have been removed.

The carbonylation reaction mixture typically produces high-boiling residues which may be tolerated, but which cannot be allowed to accumulate indefinitely. The rate at which the residues are produced and their composition will depend upon many factors, not fully understood at this time. The rate at which the residues should be removed and the level to which they are permitted to accumulate in the reaction mixture are established empirically for a particular reaction system. Typically, the reactor will be operated so that the products and other light materials will be flashed off—either from the reacting mixture itself or from a slipstream which is recycled to the reactor. In either case, heavier materials not flashed off accumulate, and a portion of these materials is separated and then concentrated to leave only the heaviest materials, which are then treated to precipitate the noble metal values according to the methods of the invention. After the noble metals have been removed, the residues may be purged.

In its broadest aspect, the invention comprises a process for recovering Group VIII noble metals from the residues of noble metal catalyzed carbonylation reactions in which esters and ethers are combined with carbon monoxide to form anhydrides or other higher molecular weight products. The process separates the residues from the carbonylation reaction mixture and then treats the residue with a suitable reagent capable of precipitating a solid containing substantially all of the noble metal content of the residue.

Separation of the residue from the carbonylation reaction mixture may be carried out by flashing of the mixture to a lower pressure and then returning the vapors to the reactor system. This may be done with the net reactor product or with a slipstream if the products are removed as vapor from the reactor itself. Any desired degree of concentration may be obtained by flashing to lower pressures. Preferably, the residue will be concentrated until substantially all of the volatile components are removed. The noble metal content will have been increased significantly, say, up to about 4 weight percent.

Reagents which have been found useful for the precipitation of noble metals from carbonylation residues include aliphatic alcohols, carboxylic acids, and carboxylic acid esters.

Of the aliphatic alcohols, those having branched chains with 3-10 carbon atoms are preferred. Isopropanol and butanols are useful. Tertiary alcohols, such as t-butyl alcohol and t-amyl alcohol, are particularly effective.

Of the carboxylic acids, those having 2-10 carbon atoms are preferred. Acetic acid is particularly effective, while propionic and n- and i-butyric acids also are useful.

The amount of reagents used will vary widely depending upon the nature of the residue, the reagents chosen, and the conditions of contacting. In the examples below, an excess of reagent was used to assure that all the rhodium was precipitated, but it will be understood that in practical applications the amount of reagent employed would be optimized. Above ambient temperatures are believed necessary for best recovery of rhodium. The contacting typically has been carried out in the examples at the atmospheric pressure boiling temperature of the treated mixture with condensation and reflux of the volatile materials to maintain the liquid composition. Typically, such reflux temperatures will be about 50° C. to 250° C. for the most useful reagents.

However, temperatures above and below the reflux temperature have been found to give acceptable results. It would be expected that an optimum temperature would be determined for practical applications of the invention. The pressure may be any suitable value, depending upon the temperature and the constituents of the system.

Various embodiments of the invention are illustrated in the following examples, in which the residue was obtained from carbonylation reactions, of which the following is a representative description.

In a continuous reaction, acetic anhydride is produced by the carbonylation of methyl acetate in the presence of methyl iodide, carbon monoxide, and hydrogen. The reaction is catalyzed by the mixture of rhodium trichloride trihydrate and lithium iodide, which are added to the initial charge placed in the reactor in amounts sufficient to provide about 0.01 mol Rh/liter of liquid in the vessel and 0.5 mol Li/mol Rh.

The reaction is operated at about 180° C., 55 kg/cm² absolute, with partial pressures of about 35 kg/cm² CO and about 5-6 kg/cm² $H_2$. The product acetic anhydride is obtained as a vapor by flashing a withdrawn stream of the reacting mixture. The remaining liquid is recycled to the reactor. The liquid recycled after flashing contains about 4 weight percent methyl iodide, 7 weight percent methyl acetate, 32 weight percent acetic anhydride, 24 weight percent acetic acid, with about 1-10 weight percent heavy residues. A slipstream is withdrawn from the recycle stream at a rate sufficient to maintain the residues in the reactor at an acceptable level. The residue-containing liquid which remains after the gases have been separated is concentrated and treated to precipitate substantially all of its rhodium content before disposal of the residue.

EXAMPLE 1

Alcohol Treatment

A 193.8-gm sample of a concentrated residue containing 0.35% rhodium, along with lithium salts and iodine, is combined with 775 gms of t-butyl alcohol and refluxed at atmospheric pressure for 6 hours. A precipitate weighing 53.7 gms is recovered and found to contain 1.4% rhodium, equaling 98.6% of the rhodium in the original residue. The rhodium remaining in the solution is 12.8 ppm by weight.

Another 20-gm sample of the concentrated residue is added to 50 gms of isopropanol and refluxed for 6 hours at atmospheric pressure. Only 0.45 gms of solids are recovered, containing 5.2% rhodium. In this test only 60.9% of the rhodium in the original residue is found in the solids. In my patent U.S. Pat. No. 4,434,240 it was suggested that isopropanol could be used as a solvent before a chemical treatment was made. However, the solvents were added at room temperature, and no precipitation of solids was observed under such conditions. Subsequently the residue and solvent were contacted with an aqueous reagent under basic conditions to precipitate solids containing rhodium. The present test shows that, under certain circumstances, isopropanol itself is a precipitating agent, although not as effective as tertiary alcohols, which are preferred.

The above results, along with those of other alcohols tested in a similar manner, are summarized in the following table.

TABLE A

| Residue gms | Alcohol | gms | Reflux hrs | Precipitate gms | % Rh (wt) | Rhodium in Filtrate wt ppm | Rhodium Recovery % |
|---|---|---|---|---|---|---|---|
| 193.8 | t-butyl | 775 | 6 | 53.7 | 1.4 | 12.8 | 98.6 |
| 20 | isopropyl | 50 | 6 | 0.45 | 5.2 | 274 | 60.9 |
| 15 | n-butyl | 60 | 6 | 0.15 | 21.6 | 307 | 58.2 |
| 41.1 | sec-butyl | 164.4 | 6 | 1.8 | 4.7 | 177 | 70.7 |
| 15 | i-butyl | 60 | 6 | 0.35 | 10.7 | 201 | 72 |
| 196.4 | t-amyl | 785.6 | 6 | 18 | 3.5 | 18.5 | 97.3 |
| 39.6 | cyclohexanol | 158.4 | 6 | 0.5 | 17.8 | 94.4 | 81.8 |

EXAMPLE 2

Solids containing 1.3 weight percent rhodium recovered from an initial treatment with t-butyl alcohol as described in Example 1 are separated and treated a second time with a second solvent to further concentrate the rhodium in the precipitated solids. The results are shown in the following table.

TABLE B

| Solids gms | Solvent | gms | Reflux hrs | Treated Solids gms | Rhodium in Solvent wt ppm | Rhodium in Treated Solids wt % |
|---|---|---|---|---|---|---|
| 3 | n-octane | 20 | 3 | 2.3 | <20.0 | 1.6 |
| 3 | water | 30 | 3 | 1.2 | <3 | 3.1 |

EXAMPLE 3

Carboxylic Acid Treatment

Samples of the concentrated residues are treated with carboxylic acids in the manner of Example 1 to precipitate solids containing rhodium, as summarized in the following table.

TABLE C

| Residue gms | Acid | gms | Reflux hrs | Precipitate gms | % Rh (wt) | Rhodium in Filtrate wt ppm | Rhodium Recovery % |
|---|---|---|---|---|---|---|---|
| 70.9 | Acetic | 283.6 | 6 | 5.4 | 6.2 | 10.2 | 99.1 |
| 20.0 | Propionic | 80 | 6 | 0.48 | 17 | <7 | >99.1 |
| 39.6 | butyric | 200 | 6 | 1.3 | 11.1 | <13 | >97.9 |
| 15.0 | i-butyric | 60 | 6 | 0.48 | 8.6 | 6 | 98.9 |

EXAMPLE 4

Solids recovered after treatment with acetic acid, as shown above in Example 3, are treated with solvents to further concentrate the rhodium in the solids, with results shown in the following table.

TABLE D

| Solids gms | Solvent | gms | Reflux hrs | Treated Solids gms | Rhodium in Solvent wt ppm | Rhodium Recovery % |
|---|---|---|---|---|---|---|
| 1 | MeOAc* | 12.5 | 3 | 0.45 | 10.4 | 99.8 |
| 1 | Toluene | 25 | 3 | 0.43 | 6.3 | 99.7 |
| 1 | Cyclohexane | 25 | 3 | 0.56 | <5 | <99.9 |
| 1 | THF** | 25 | 3 | 0.41 | 28.3 | 98.1 |

*Methyl acetate
**Tetrahydrofuran

Combinations of reagents may be used, as illustrated in the following example.

EXAMPLE 5

Treatment with Mixtures

A sample of residue is treated with acetic acid plus another reagent in a manner similar to Examples 1 and 3, with the following results.

TABLE E

| Residue gms | Acetic Acid gms | Second Reagent | gms | Reflux hrs | Precipitate gms | Precipitate % Rh (wt) | Rhodium in Filtrate wt ppm | Rhodium Recovery % |
|---|---|---|---|---|---|---|---|---|
| 20 | 40 | cyclohexane | 40 | 6 | 0.55 | 15.3 | 4.2 | 99.3 |
| 20 | 40 | n-octane | 40 | 6 | 0.8 | 15.5 | <3 | >99.8 |
| 20 | 40 | acetic anhydride | 40 | 6 | 1.2 | 8.4 | 31.8 | 96.9 |
| 25.1 | 50.2 | methyl acetate | 50.2 | 6 | 1.6 | 3.1 | 153 | 72.7 |
| 10 | 20 | water | 20 | 6 | 3.7 | 1.3 | <5 | >99.4 |

EXAMPLE 6

Carboxylic Acid Ester Treatment

A sample of residue is treated with carboxylic acid esters in the manner of Examples 1 and 3 to precipitate solids containing rhodium, with the results summarized in the following table.

TABLE F

| gms | Ester | gms | Reflux hrs | Precipitate gms | Precipitate % Rh (wt) | Rhodium in Filtrate wt ppm | Rhodium Recovery % |
|---|---|---|---|---|---|---|---|
| 15 | methyl acetate | 60 | 6 | 1.2 | 0.06 | 737 | <1 |
| 15 | n-butyl acetate | 60 | 6 | 1.2 | 2.9 | 16.1 | 95.6 |
| 15 | ethylidene diacetate | 60 | 6 | 1.6 | 3.3 | 23.8 | 97.0 |

The above results suggest that esters containing alkyl groups larger than the methyl group can provide good recovery of rhodium from the residue.

EXAMPLE 7

The use of the solids produced by the treatment of the invention is illustrated in the following test, in which 11 grams of solids containing 2.3 weight percent rhodium are substituted for a pure rhodium compound. The solids are obtained by treating a residue containing 0.3 weight percent rhodium with acetic acid, as described in Example 1.

To a 1-liter Hastelloy B autoclave is charged 240 grams of methyl acetate, 82 grams of acetic acid, 155 grams of methyl iodide, 30.5 grams of lithium iodide, and 11 grams of the solids described above. The mixture is reacted for 2 hours at 180° C. and 49.3 bar carbon monoxide pressure, after which it is found that 93.6% of the methyl acetate has been converted with a 93.0% selectivity to acetic anhydride. Thus, it is concluded that the solids containing rhodium performed in a generally similar manner to pure rhodium compounds.

EXAMPLE 8

The sole FIGURE presents a simple block diagram illustrating an embodiment of the invention. A 101.7-gm sample of heavy residue (10) containing 0.26 wt. % rhodium is contacted (14) at reflux conditions with 406.8 gms acetic acid (12) for 6 hours. The precipitated solids are filtered out of the solution (16). They total 12.9 gms, having 2% rhodium, or 97.8% of the rhodium in the original sample. The filtrate, which contains 13.5 wt. ppm rhodium, is distilled (18) to remove the acetic acid at 60° C. and 0.5 torr, leaving 77.3 gms of solids containing 75 wt. ppm rhodium (20). These solids are dissolved in 100 gms of methyl iodide and 50 gms of 50% aqueous HI (22), which extracts (24) the rhodium content into the aqueous layer, while the methyl iodide layer contains most of the organic materials from the solids. The methyl iodide layer is separated and extracted again with two 37.5-gm portions of 50% aqueous HI. After the third extraction, the methyl iodide layer is distilled (26) at room temperature and 0.5 torr to leave 43 gms of solids (28) containing 46.1 wt. ppm rhodium, equal to about 0.8% of the original rhodium. The aqueous HI layers (30) contain about 1.5% of the original rhodium. These are recycled to the carbonylation reactor as shown or, alternatively, are concentrated by distilling off the HI-H$_2$O azeotrope before recycling. The precipitated solids are given a secondary treatment (32) with 325 gms of cyclohexane to remove additional organic materials. The solids are filtered again, and the concentrated solids, now containing 4 wt. % rhodium, are recycled (34) to the carbonylation reactor, while the filtrate (3) containing only 2 wt. ppm rhodium is sent to solvent recovery (not shown) and the solids disposed of.

What is claimed is:

1. A process for recovering rhodium from the high molecular weight residues containing organic carbonyl and acetate functions formed in rhodium-lithium catalyzed carbonylation reactions in which esters and ethers are combined with carbon monoxide in the presence of iodides to form anhydrides, comprising:

(a) separating and concentrating the residue from the carbonylation reaction mixture by removing volatile components thereof;

(b) treating at temperatures above ambient the separated residue of (a) with a reagent capable of precipitating a solid containing substantially all of the rhodium content of said residue and consisting of at least one member of the group consisting of, cyclohexanol, tertiary aliphatic alcohols, and carboxylic acid esters from the group consisting of butyl acetate and ethylidene acetate; and (c) separating the precipitated solid of (b).

2. A process of claim 1 further comprising:

(d) returning said solid separated in (c) to the carbonylation reaction mixture for reuse.

3. A process of claim 1 wherein said treatment is carried out at a temperature in the range of 50° C. to 250° C.

4. A process of claim 2 wherein said separated solid of (c) is treated with at least one solvent selected from the group consisting of alkanes, cycloalkanes, aromatics, ethers and cyclic ethers, to concentrate the rhodium values by removing a portion of the organic content of said solids.

5. A process of claim 1 wherein said tertiary aliphatic alcohol is t-butyl alcohol or t-amyl alcohol.

6. A process of claim 1 further comprising the steps of:

(e) distilling the treated liquid residues recovered after removal of the precipitated solids containing rhodium in (c), thereby concentrating the liquid residues;

(f) extracting said distilled residues of (e) with methyl iodide and aqueous hydrogen iodide to dissolve a portion of the rhodium content;

(g) and recovering an aqueous layer with dissolved rhodium.

* * * * *